United States Patent
Connors

(10) Patent No.: US 9,244,027 B2
(45) Date of Patent: Jan. 26, 2016

(54) METHOD AND INSTRUMENT FOR IDENTIFYING JEWELRY WITH PLATED ELEMENT USING X-RAY FLORESCENCE

(71) Applicant: Brendan Connors, San Diego, CA (US)

(72) Inventor: Brendan Connors, San Diego, CA (US)

(73) Assignee: OLYMPUS NDT, Waltham, MA (US)

( * ) Notice: Subject to any disclaimer, the term of this patent is extended or adjusted under 35 U.S.C. 154(b) by 228 days.

(21) Appl. No.: 13/906,641

(22) Filed: May 31, 2013

(65) Prior Publication Data
US 2013/0322595 A1    Dec. 5, 2013

Related U.S. Application Data

(60) Provisional application No. 61/653,820, filed on May 31, 2012.

(51) Int. Cl.
*G01N 23/223* (2006.01)
(52) U.S. Cl.
CPC ........ *G01N 23/223* (2013.01); *G01N 2223/076* (2013.01)

(58) Field of Classification Search
CPC .......... G01N 23/223; G01N 2223/076; G01N 23/2076; G01N 23/22; G01N 23/2204; G01N 2223/633; G01N 2223/308; G01N 2223/315; G01B 15/02; C08J 2367/02; C08J 5/18; C08J 2367/00; C08J 2483/00; C08J 7/047; C08J 7/123; A01G 9/1438; A47F 5/00; A61J 17/00; A61M 1/16; G02B 1/105
USPC ....................................... 378/45, 48
See application file for complete search history.

(56) References Cited

U.S. PATENT DOCUMENTS

2013/0202083 A1\*  8/2013  Piorek et al. ................... 378/45

\* cited by examiner

*Primary Examiner* — Irakli Kiknadze
(74) *Attorney, Agent, or Firm* — Ostrolenk Faber LLP

(57) ABSTRACT

The method uses an XRF instrument for identifying a specified element on a jewelry sample by illuminating its surface with excitation radiation and measuring first and second intensities of characteristic emission lines of a specified element and calculating the ratio between the intensities to establish a measured thickness and to determine based on a certain range criteria whether the sample can be considered to be plated jewelry.

20 Claims, 6 Drawing Sheets

| Customer name | | optional |
|---|---|---|
| Customer phone | | optional |
| Date and Time of testing | | |
| Jewelry category | | Options are: Bracelet, chains, wire stock, watches, pens |
| Picture requested | | |
| Paper report requested | | |

Fig. 4

Typical Gold Plating Applications and Thicknesses chart c-1: "Gold Filled" Finishes

| Item category | Layer thickness microns | Layer thickness microinches | Estimated Durability in years |
|---|---|---|---|
| belt buckle | 40 - 70 | 1574 - 2952 | 5 - 10 |
| bracelets | 30 - 75 | 1181 - 2962 | 5 - 10 |
| chains | 5 - 10 | 196 - 393 | 2 - 8 |
| cuff links | 20 - 40 | 787 - 1574 | 5 - 8 |
| eye frames | 10 - 20 | 393 - 787 | 5 - 8 |
| pens | 20 - 40 | 787 - 1574 | 5 - 15 |
| wire stock | 15 - 45 | 590 - 1771 | 7 - 10 |
| watches | 50 - 120 | 1968 - 4724 | 10 - 35 | chart c-2: "Gold Electroplated" Finishes

| Item category | Layer thickness microns | Layer thickness microinches | Estimated Durability in years |
|---|---|---|---|
| belt buckle | 2.5 - 8.0 | 98 - 314 | 2 - 5 |
| bracelets | 2.5 - 8.0 | 98 - 314 | 3 - 7 |
| chains | 0.5 - 2.5 | 19 - 98 | 1 - 3 |
| cuff links | 2.5 - 5.0 | 98 - 196 | 2 - 5 |
| eye frames | 1.0 - 2.5 | 39 - 98 | 1 - 3 |
| pens | 2.5 - 5.0 | 98 - 196 | 2 - 7 |
| wire stock | - - | - - | - - |
| watches | 5.0 - 20.0 | 196 - 787 | 10 - 35 |

Fig. 5

METHOD AND INSTRUMENT FOR IDENTIFYING JEWELRY WITH PLATED ELEMENT USING X-RAY FLORESCENCE

CROSS-REFERENCE TO RELATED APPLICATION

This application claims the benefit and priority of U.S. Provisional patent application Ser. No. 61/653,820 filed May 31, 2012 entitled A METHOD AND INSTRUMENT FOR IDENTIFYING JEWELRY WITH PLATED ELEMENT USING X-RAY FLORESCENCE, the entire disclosure of which is incorporated herein by reference.

FIELD OF THE INVENTION

The present invention relates to testing, characterization and identification of materials using x-ray florescence, more particularly to a method and instrument for identifying jewelry with a plated element using x-ray florescence technologies.

BACKGROUND OF THE INVENTION

Jewelry identification and testing has long been a challenge in the human history. The challenges, among others, are mainly to identify if a target test piece contains certain desirable alloys, and if so, the concentration and thickness of each of them, and further if the desirable elements are present in the bulk of the test piece or are merely plated on the surface of the test piece.

In the last few decades, x-ray florescence (XRF) technologies have been more often used for jewelry analysis. XRF is now a widely used, proven, and accepted method of chemistry analysis and used in karating of precious metals samples, including for purity and fineness. XRF analysis provides a less expensive, quicker testing alternative to fire assay and chemical tests, and on-the-spot analysis of silver, platinum, or other materials, making it an easy way to boost customer confidence and ensure dealer reliability.

However, a method and instrument for accurate and fast identification of whether a piece of jewelry is plated with certain precious metal has seen lagging the market needs. The challenges remain due to a few considerations, among them, the need to address deviating standard of thickness or cut-off threshold for defining whether a piece of jewelry is plated or not. For example, the thickness of identified gold on the surface of necklace in a range of 5 to 10 micron would render the conclusion that the necklace is gold plated. However, for bracelets, the same thickness of 5 to 10 microns might not render the same conclusion that the bracelets are gold-plated.

Some prior teachings shown to use XRF for measuring concentrations of certain elements, in surface-covering layers, such as paint, can be found with reference to U.S. Patents, for example, U.S. Pat. Nos. 5,396,529 and 7,702,067, both by Grodzins, (herein collectively as "Grodzins"). Grodzins teaches measurement of the concentration of lead in paint on the basis of inducing and detecting fluorescence of the x-rays of lead.

The contents of the foregoing Grodzins U.S. Pat. Nos. 5,396,529 and 7,702,067 are incorporated herein by reference.

The previous teachings as mentioned above all include the following steps using XRF for identifying a specified element on the surface of an object:

a. illuminating a surface of the sample with x-ray excitation radiation;

b. measuring a first intensity of a characteristic emission line of the specified element at a first energy;

c. measuring a second intensity of a characteristic emission line of the specified element at a second energy;

d. calculating the ratio between the first intensity to the second intensity to establish the possible thickness of the specified element disposed above the bulk of the sample.

It therefore can be understood that the thickness can be quite accurately measured in existing practice as discussed above. However, existing methods do not address sufficiently what the measured thickness should be compared to, in order to obtain a confident conclusion whether the sample is to be considered plated with the precious metal or not. A predetermined cut-off thickness threshold to determine whether the sample meets the criterion qualifying the sample to be considered to be plated needs to be further defined for each functional category, i.e., chains, bracelets; and for each types of metal, i.e., silver, gold, etc. Therefore, an improved method and instrument is needed to more accurately and confidently provide customers with a reliable indication and/or quantitative measure indicative of whether a piece of jewelry is plated with the desirable metal or is not.

SUMMARY OF THE INVENTION

In accordance with one aspect of the present invention, an x-ray fluorescence spectrometer is provided for determining a concentration of a specified element. The spectrometer has a source of x-ray excitation for illuminating a surface of a sample and a detector for measuring a first intensity of a first characteristic emission line of the specified element at a first energy and a second intensity of a second characteristic emission line of the specified element at a second energy, and for outputting a detector signal corresponding to each of the first and second intensities. The spectrometer also has a signal processor for comparing the first intensity to the second intensity to establish the thickness of the specified element, if it determines there is any.

In accordance with a further aspect of the present invention, the spectrometer further has a jewelry thickness threshold comparison module, preferably residing in and configured to be executed by the processor, and provides a table containing empirical data of predetermined thickness threshold range for many functional categories of jewelry and for each commonly used precious metal type. The threshold comparison module then compares the measured thickness to the table values for its corresponding category to determine whether the sample meets the criterion qualifying the sample to be considered plated.

In accordance with yet another aspect of the invention, the thickness threshold module as an executable computer program, can alternatively reside in a medium separate from the digital processor, and is readable and executable by the digital processor of any existing spectrometer.

The advantages, among others, include much improved capability of more accurately and confidently providing customers with the conclusion whether a piece of jewelry is plated with the desirable metal and/or whether it does not meet the criteria for being considered plated.

BRIEF DESCRIPTION OF THE DRAWINGS

FIG. 4 is a table chart used with the invention.

FIG. 5 shows an exemplary table containing typical thickness ranges for different functional categories of the present invention.

DETAILED DESCRIPTION OF THE INVENTION

Figure 1:
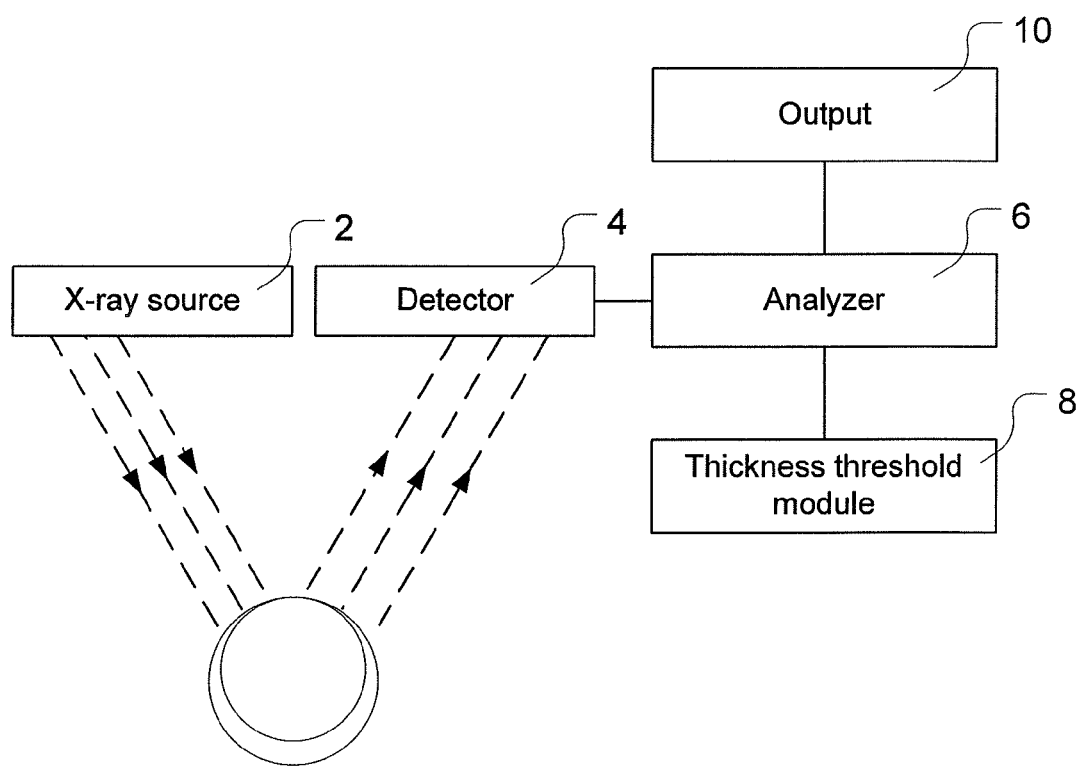
FIG. 1 is a block diagram of the invention.

FIG. 1 illustrates an XRF instrument having a source 2 of x-ray excitation for illuminating a surface of a sample 1 and a detector 4 for measuring a first intensity of a first characteristic emission line of the specified element, such as gold, at a first energy and a second intensity of a second characteristic emission line of an alternative element at a second energy, and for outputting a detector signal corresponding to each of the first and second intensities. The spectrometer also has a digital data processor, or analyzer, 6, for comparing the first intensity to the second intensity to establish the thickness of the specified element, if it determines there is any. A result of the comparisons, in alphanumeric or pictorial format or formats, can be outputted to any display device (not shown) via the output module 10.

FIG. 1 further shows that the XRF instrument also comprises a jewelry thickness threshold comparison module 8, preferably residing in and configured to be executed by processor 6, that provides a table containing empirical data of predetermined thickness threshold ranges for many functional categories of jewelry and for each commonly used precious metal type. The threshold comparison module 8 then compares the measured thickness to the table for its corresponding category to determine whether the sample meets the criterion qualifying the sample to be considered plated.

It should be noted the thickness threshold module described above as an executable computer program, can alternatively reside in a medium separate from the digital processor 6, and be readable and executable by the digital processor 6. The digital processor can be newly designed according to the present invention, or comprise any existing processor in an existing XRF analyzer. It can also be implemented in any form commercially known, such as a FPGA (Field Programmable Gate Array) or DSP (Digital Signal Processor), which all falls within the scope of present invention.

Figure 2:
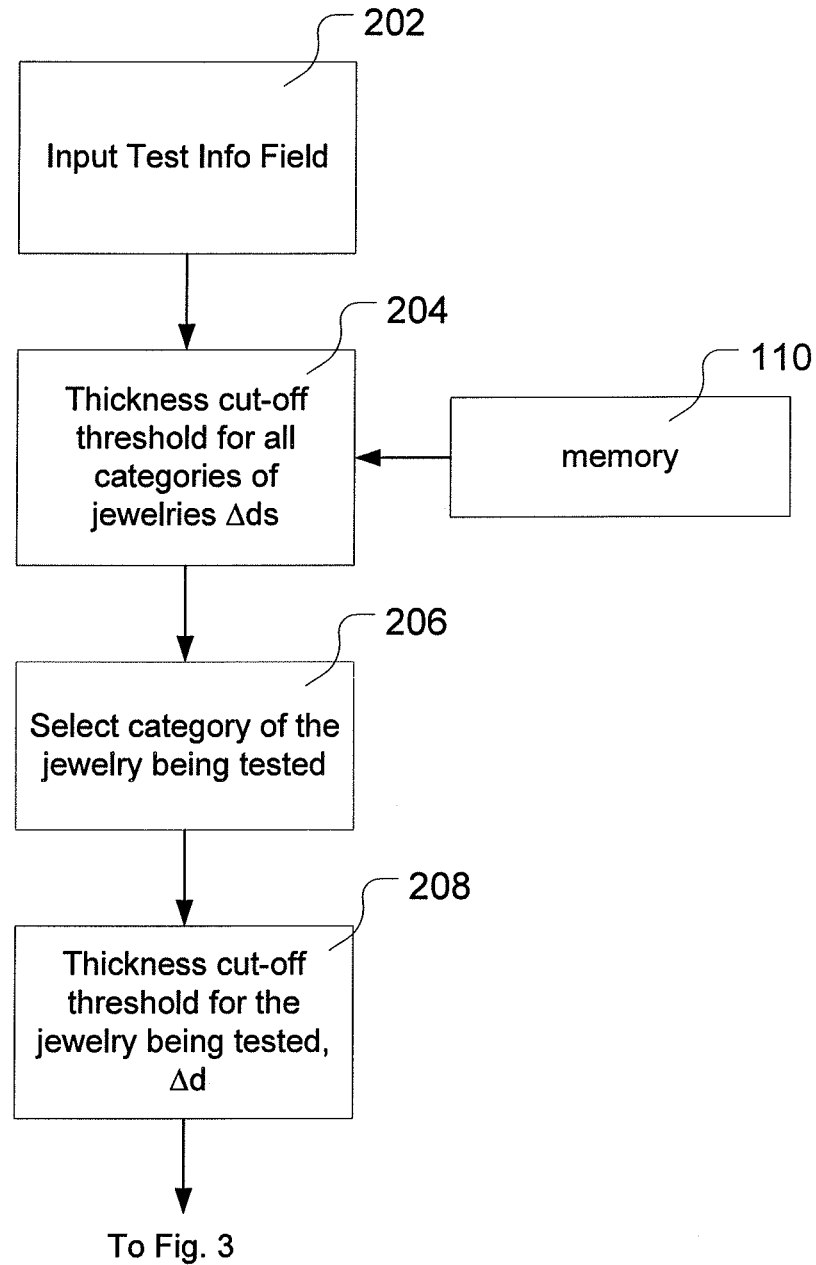
FIG. 2 is a schematic diagram showing initialization steps of the instrument of the invention.

FIG. 2 is a schematic diagram showing the steps preparing the instrument with a table containing thickness cut-off threshold data for commonly used jewelry according to the present disclosure. In FIG. 1, in step 202, one can import an existing table containing empirical data for typical ranges of thickness for typical functional categories of jewelry from a memory 110. An example of such table is shown in FIG. 5. In step 204, the thickness cut-off thresholds of all categories of jewelry are made available for the instrument.

Further in FIG. 2, the preferred embodiment includes a "customer registry" form 402, preferably presented on the user interface, an example of which is shown in FIG. 4. The form 402 allows users to specify the functional category of the jewelry being tested, such as, a necklace, a bracelet, etc. In step 206 of FIG. 2, the input of a category of the jewelry sample is provided to the instrument. In step 208, the predetermined thickness range Δd specifically for the selected functional category jewelry and for the predetermined kind of metal is calculated by the instrument.

It should be noted that the above functions can be loaded onto digital data processor 6 as shown in FIG. 1 via a "threshold module", which is executable by the digital data processor 6.

Figure 3:
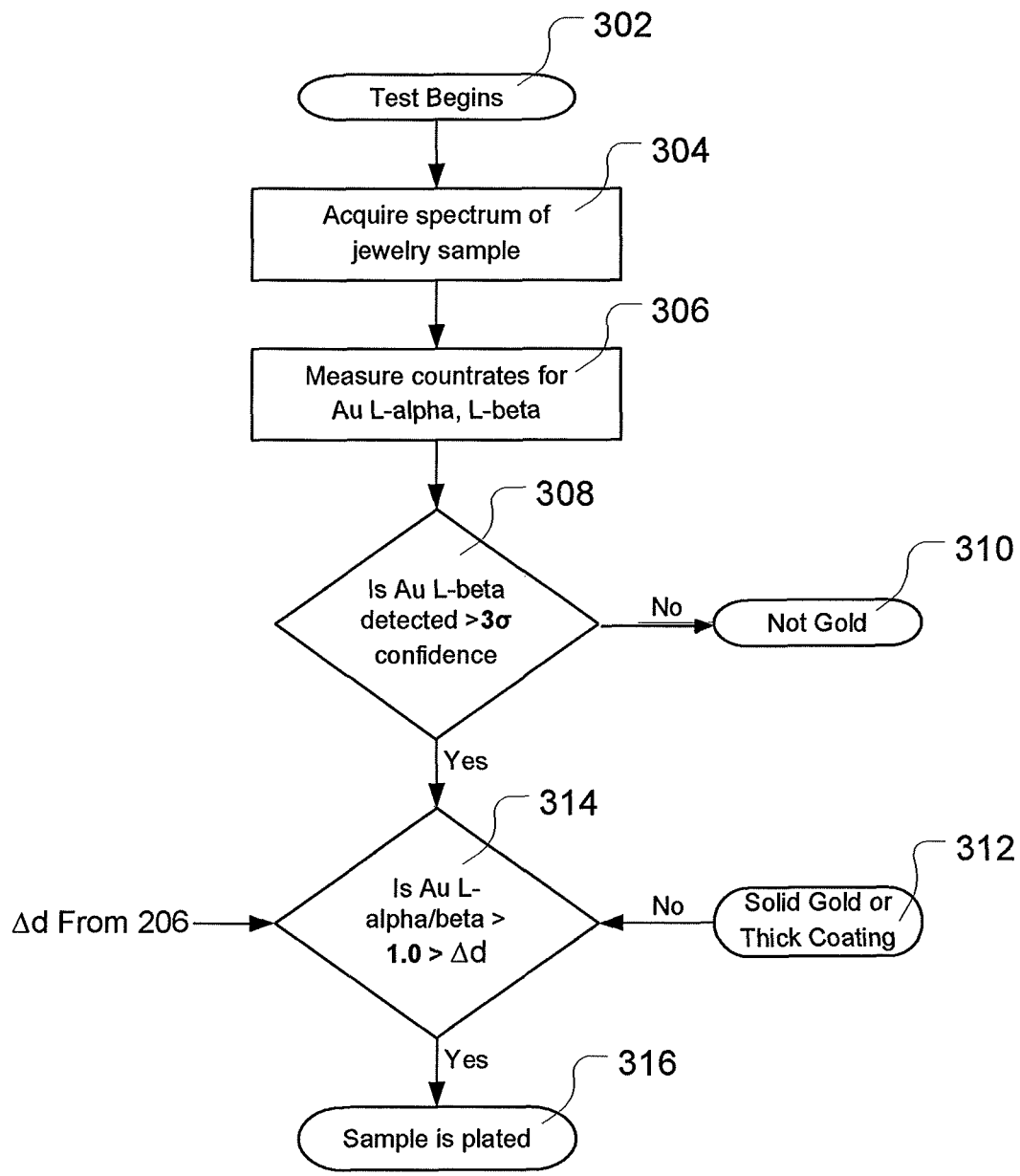
FIG. 3 is a flow diagram showing operational steps of the instrument of the invention.

FIG. 3 is a schematic diagram showing the steps the instrument, preferably the steps digital processor 6 executes for measuring a jewelry sample, with predetermined jewelry functional category and the subsequent thickness range Δd as defined in step 208 of FIG. 2.

More specifically in FIG. 3, after the input of customer registry form 402, such as that shown in FIG. 4, and the preparation of the corresponding thickness ranges prepared in FIG. 2, a test begins at step 302 by outputting XRF energy. In step 304, the instrument acquires a jewelry sample spectrum signal as in XRF testing processes typically performed for this type of testing. In step 306, for an example case where gold is the predetermined metal to identify, Au L-alpha and L-beta are detected and corresponding data are acquired. In step 308, line ratio L-alpha and L-beta is calculated according to the corresponding data, which is a process typically done in line ratio calculation. Also in step 308, based on the L-beta value, if it can be determined the specimen contains gold (solid or plated), the process proceeds to step 314. If it can be determined the specimen does not have gold, it proceeds to step 310 and an analyzing process is ended.

Further, in FIG. 3, in step 314, line ratio between L-alpha and beta is calculated and the thickness of the plating material is determined. If the thickness of the plated material is larger than a predetermined value Δd for the specific metal, such as gold, it can be determined, in step 312, that the specimen is solid gold or that it has a thick coating.

Note that Δd is the thickness threshold value obtained from the thickness module shown in FIG. 2 and is specific for the functional category of the jewelry and specific to the type of precious metal.

In step 314, if the thickness falls within the range of specific Δd, the instrument will yield the conclusion that the specimen is plated with the detected precious metal.

Reference is now made to FIG. 4, which shows an exemplary customer request form 402 shown on the interface of the instrument, allowing a customer or service representatives to input the "jewelry category" and various information. The data from customer's input of jewelry category is used to sort and retrieve the specific thickness threshold range for step 206 in FIG. 2.

Referring now to FIG. 5, the exemplary table 502 contains the typical range of thickness for a number of typical functional categories of gold plated jewelry. As can be appreciated similar data can be provided for the table according to the preferred embodiment for other types of precious metals, such as silver and platinum.

Also worth noting that, in FIG. 5, Δd for each functional category has both an upper and a lower threshold. The upper range denotes the separation line between solid gold or thick gold, on the one hand, and plated gold, on the other. The lower range denotes the separation line between plated gold or not plated (too little plating to be considered plated).

Figure 6:
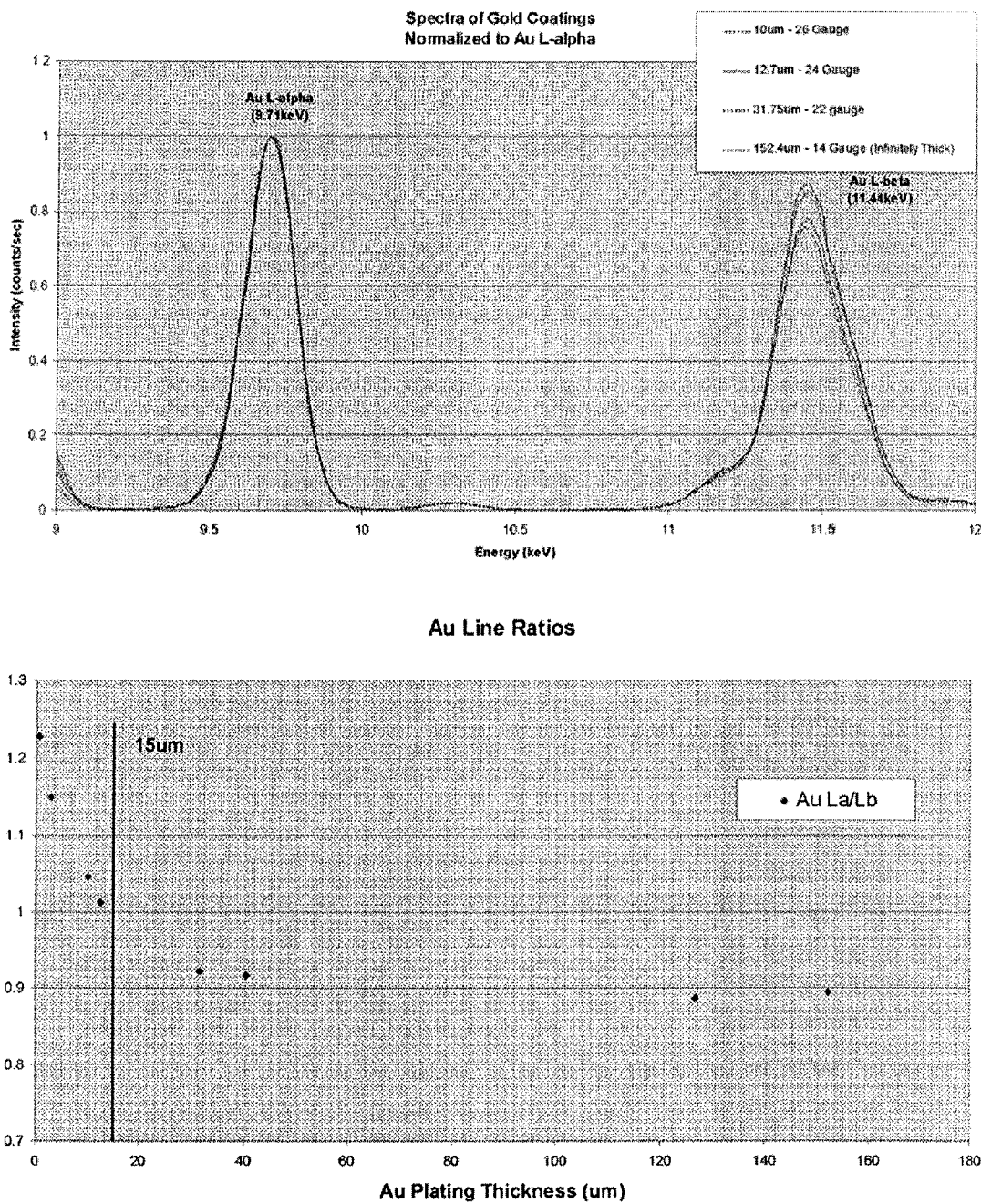
FIG. 6 shows diagrams produced with the invention for the purposes of determining thicknesses of target elements.

FIG. 6 shows diagrams obtained with conventional XRF processes for determining line ratios and subsequently determining thicknesses of the target elements. It is a known practice in the XRF industry that can be used by the present invention, preferably in steps 304-308 in FIG. 3.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method using an XRF instrument for identifying a specified element in and on the surface of a jewelry sample, the method comprising the steps of:
   a. illuminating a surface of the sample with x-ray excitation radiation;
   b. measuring a first intensity of a characteristic emission line of the specified element at a first energy;
   c. measuring a second intensity of a characteristic emission line of the specified element at a second energy;
   d. calculating the ratio between the first intensity to the second intensity to establish a measured thickness of the specified element disposed above a bulk of the sample;
   e. inputting a functional category of the jewelry sample; and
   f. comparing the measured thickness to thickness threshold data for the corresponding category of the sample to determine whether the sample meets the criterion to be considered plated jewelry.

2. The method of claim 1, wherein the measuring steps comprise measuring x-ray fluorescence.

3. The method of claim 1, including providing the thickness threshold data in a table and accessing the table during the comparing step to determine whether the sample meets the criterion.

4. The method of claim 3, wherein the table is provided with a plurality of item categories.

5. The method of claim 4, wherein the item categories include two or more of the following item categories: belt buckles; bracelets; chains; cufflinks; eyeframes; pens; wirestock; and watches.

6. The method of claim 5, wherein the table is provided with plating thickness ranges for samples that are formed with gold-filled finishes.

7. The method of claim 5, wherein the table is provided with plating thickness ranges for samples that are formed with electrical gold plating.

8. The method of claim 3, including providing an x-ray processor and providing the table separately from the processor.

9. The method of claim 1, including enabling a user to input jewelry sample categories.

10. The method of claim 1, including measuring L-alpha and L-beta parameters for gold.

11. The method of claim 1, including providing a user interface comprising a facility for inputting at least a jewelry category field and a date and time of testing field.

12. The method of claim 11, including enabling the user interface to input two or more of a customer name, a customer telephone number, whether a picture is requested and whether a paper report is being requested.

13. An XRF instrument for identifying a specified element in and on the surface of a jewelry sample, comprising:
   a. at least one x-ray source configured to illuminate a surface of the sample with x-ray excitation radiation;
   b. at least one detector configured to measure a first intensity of a characteristic emission line of a specified element at a first energy and a second intensity of a characteristic emission line of the specified element at a second energy;
   c. an analyzer for calculating the ratio between the first intensity and the second intensity to establish a measured thickness of the specified element disposed above the bulk of the sample;
   d. an input device for specifying a functional category of the jewelry sample; and
   e. a thickness threshold module executable by the analyzer and associated with a thickness threshold data table for sorting and determining a threshold range for the corresponding category of the sample,
   wherein the analyzer is configured to compare the measured thickness with the threshold range to determine whether the sample meets a criterion for qualifying the sample as plated or not.

14. The XRF instrument according to claim 13, wherein the thickness threshold module resides in and is configured to be executed by the analyzer.

15. The XRF instrument according to claim 13, wherein the thickness threshold module is an executable computer program, residing in a medium separate from the analyzer, and is readable and executable by the analyzer.

16. The XRF instrument according to claim 13, wherein the thickness threshold data table is configured to hold therein item categories including two or more of the following item categories: belt buckles; bracelets; chains; cuff links; eye frames; pens; wire stocks; and watches.

17. The XRF instrument according to claim 13, wherein at least one detector is configured to measure L-alpha and L-beta parameters for gold.

18. The XRF instrument according to claim 13, including a user interface comprising a facility for inputting at least a jewelry category field and a date and time of testing field.

19. The XRF instrument according to claim 18, wherein the user interface enables inputting two or more of a customer name, a customer telephone number, whether a picture is requested and whether a paper report is being requested.

20. The XRF instrument according to claim 13, wherein at least one x-ray source is configured produce x-ray fluorescence.

* * * * *